United States Patent
Gentz et al.

(10) Patent No.: US 8,491,511 B2
(45) Date of Patent: Jul. 23, 2013

(54) ORTHOTIC JOINT HAVING TWO FUNCTION MEANS FOR FORMING A RESILIENT DORSAL ABUTMENT AND A RESILIENT PLANTAR ABUTMENT

(75) Inventors: Ralf Gentz, Mechtersen (DE); Jorg Fior, Luneburg (DE)

(73) Assignee: Fior & Gentz GmbH (DE)

( * ) Notice: Subject to any disclaimer, the term of this patent is extended or adjusted under 35 U.S.C. 154(b) by 177 days.

(21) Appl. No.: 13/080,478

(22) Filed: Apr. 5, 2011

(65) Prior Publication Data

US 2011/0251539 A1   Oct. 13, 2011

(30) Foreign Application Priority Data

Apr. 7, 2010 (DE) .......................... 10 2010 014 334

(51) Int. Cl.
*A61F 5/00* (2006.01)
(52) U.S. Cl.
USPC ..................... 602/16; 602/20; 602/23; 602/26
(58) Field of Classification Search
USPC ..................... 602/5, 16, 29–28; 128/878–879, 128/882; 5/624
See application file for complete search history.

(56) References Cited

U.S. PATENT DOCUMENTS

| 4,489,718 A | 12/1984 | Martin |
| 4,522,199 A | 6/1985 | Waddell et al. |
| 4,771,768 A | 9/1988 | Crispin |
| 7,044,926 B2 * | 5/2006 | Carlson .......................... 602/27 |
| 2005/0187505 A1 * | 8/2005 | Carlson .......................... 602/23 |

FOREIGN PATENT DOCUMENTS

WO   2008080231 A1   7/2008

OTHER PUBLICATIONS

Office Action dated Jan. 19, 2011 from German Patent Application No. 10 2010 014 334.0-51 filed Apr. 7, 2010 (8 pages).

* cited by examiner

*Primary Examiner* — Michael A. Brown
(74) *Attorney, Agent, or Firm* — Schmeiser, Olsen & Watts, LLP

(57) ABSTRACT

The invention relates to an orthotic joint, in particular ankle joint for a leg orthosis, comprising a joint part with a splint mounting and a stirrup which is connected to the joint part to be pivotable about an axis A and has a dorsal and a plantar abutment surface wherein on both sides of the axis A, on the joint part is formed a channel, in which one function means, each, for forming a dorsal or plantar abutment for the stirrup or its abutment surfaces is arranged, which is characterized in that each function means comprises a cup spring arrangement.

12 Claims, 4 Drawing Sheets

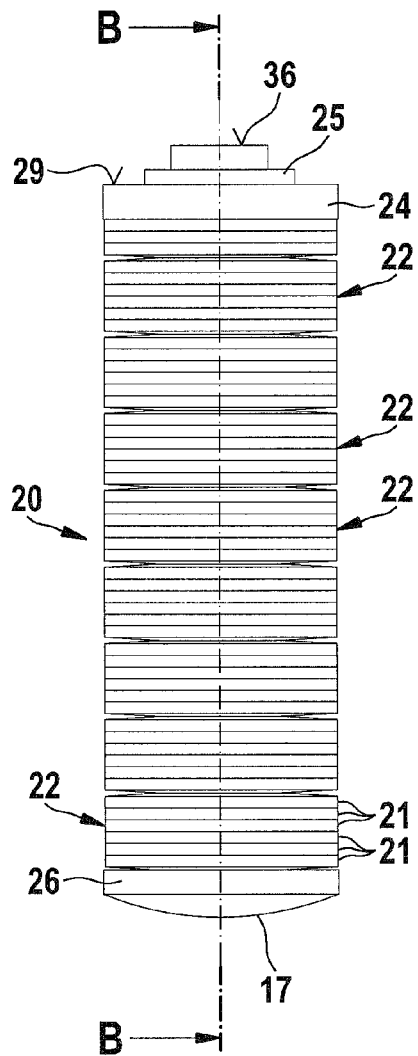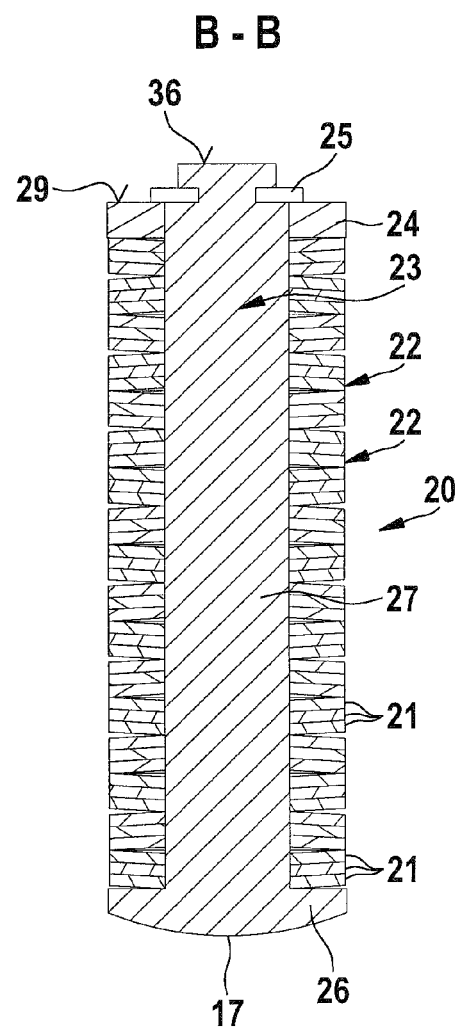

ORTHOTIC JOINT HAVING TWO FUNCTION MEANS FOR FORMING A RESILIENT DORSAL ABUTMENT AND A RESILIENT PLANTAR ABUTMENT

The invention relates to an orthotic joint, in particular ankle joint for a leg orthosis, comprising a joint part with a splint mounting and a stirrup which is connected to the joint part to be pivotable about an axis and has a dorsal and a plantar abutment surface, wherein on both sides of the axis on the joint part is formed a channel in which one function means each for forming a dorsal or plantar abutment for the stirrup or its abutment surfaces is arranged.

Such orthotic joints preferably serve in orthopaedics for the formation of lower leg orthoses which are also known as "Ankle Foot Orthosis" (AFO). The orthotic joints serve to stabilise the natural joints. These orthotic joints are used in particular for patients with infantile cerebral paresis or comparable disorders or impairments. These disorders usually have a typical paralysis picture, which leads to shortening of the tendons, in particular in the ankle region, and to shortening of the knee-bending and hip-bending tendons. In order to nevertheless facilitate a gait pattern as natural as possible for the patient, the corresponding tendons are extended by way of an operation. After the operation, the use of orthotic joints is necessary on one or both sides, using the example of the ankle joint, on one side of the ankle (inside or outside) or on both sides of the ankle (inside and outside). The ankle joint is thereby initially completely locked to guarantee the patient a secure standing position. In the standing position, the angle between the foot and the lower leg is about 90°, wherein the angle for slight forward leaning of the patient may also be slightly less than 90°, that is for example 85°, and for a slight backward leaning position of the patient also slightly greater than 90°, that is for example 95°. Independently of the size of the angle, that is independently of whether the patient is completely upright or is standing leaning slightly forwards or backwards, the standing position of the patient is referred to as the plumb line. This initial position is also called function position. The task of the orthotic joints is to maintain this function position against the weight of the patient. There is the further requirement to gradually increase the freedom of movement in the joint or orthotic joint to gradually reach the natural gait pattern. In order to facilitate a natural gait pattern, a dorsal extension of about 10° and a plantar flexion of about 15° are necessary starting from the function position.

Hence, the locking is released bit by bit, wherein the movement is to be released against a counter-force, so that via the counter-force the lower leg of the patient is again and again brought to the function position for a secure standing position of the patient.

In order to meet these requirements, that is on the one hand stability in the standing position of the patient and on the other hand allowing movement in the joint or orthotic joint, different embodiments are used in practice. One possibility exists in using carbon springs in the lower leg orthosis which run from the sole behind the heel and behind the Achilles tendon to behind the calf. These carbon springs formed as flat springs are however, if considerable forces are to be absorbed, very wide and thick so that integration into the orthosis is possible only with difficulty. Furthermore, the arrangement of the carbon springs is anatomically unfavourable, since the point of rotation lies behind the axis of rotation of the natural joint. Orthotic joints having the features of the preamble of claim 1 are known, in which usually helical springs are used as function means which are known from the field of dorsiflexion foot joints. The helical springs are arranged in the channel and cooperate either directly or via a bolt or the like with the stirrup or its abutment surfaces. However, it has been shown that the helical springs used hitherto are not adequate to apply the counter-force to press the lower leg back into the function position after dorsal extension or plantar flexion. Even if the spring force of these helical springs is increased, the counter-force is not adequate. Moreover, due to the larger dimensions of the helical springs, the construction size of the orthotic joint becomes very large, which reduces the wearer comfort.

The object is therefore to provide an adjustable and compact orthotic joint which has adequate dimensions to bring the lower leg of the patient against his body weight into a starting position or function position.

This object is achieved by an orthotic joint of the type mentioned in the introduction in that each function means comprises a cup spring arrangement. Cup springs are characterised in that they produce a very high spring force on a very short spring path. With the design according to the invention, an orthotic joint is provided in surprisingly simple manner which on the one hand provides adequate spring force to press the lower leg of the patient into the function position. On the other hand the design according to the invention facilitates adjustment of the movability of the orthotic joint, that is step-wise change of the freedom of movement of the joint or orthotic joint, wherein the movement is effected against a high spring force. A resilient dorsal abutment and a resilient plantar abutment are thus provided by the cup spring arrangements.

An advantageous development of the invention is characterised in that the cup spring arrangement consists of several cup spring packets, wherein each cup spring packet is formed from several cup springs. The spring force is thus particularly high so that the return of the lower leg against the weight of the patient into the function position is reliably ensured.

Each function means advantageously comprises an adjusting element for adjusting the freedom of movement and an adjusting means for adjusting the plumb line. Due to the adjusting element for adjusting the freedom of movement, the step-wise change of movements, that is dorsal extension and/or plantar flexion, is facilitated in addition to the completely blocked movement of the joint or orthotic joint. In other words, the front, dorsal abutment and the rear, plantar abutment may be adjusted. The initial position or neutral function position may be changed using the adjusting element for adjusting the plumb line, and specifically independently of the adjustment with regard to the freedom of movement.

Further suitable and/or advantageous features and developments can be seen from the sub-claims and the description. A particularly preferred embodiment of the invention is illustrated in more detail using the attached drawing. In the drawing:

FIG. 5 shows a front view of a clamping unit as a component of the function means, and FIG. 6 shows the clamping unit according to FIG. 5 in section along B-B.

Figure 1:
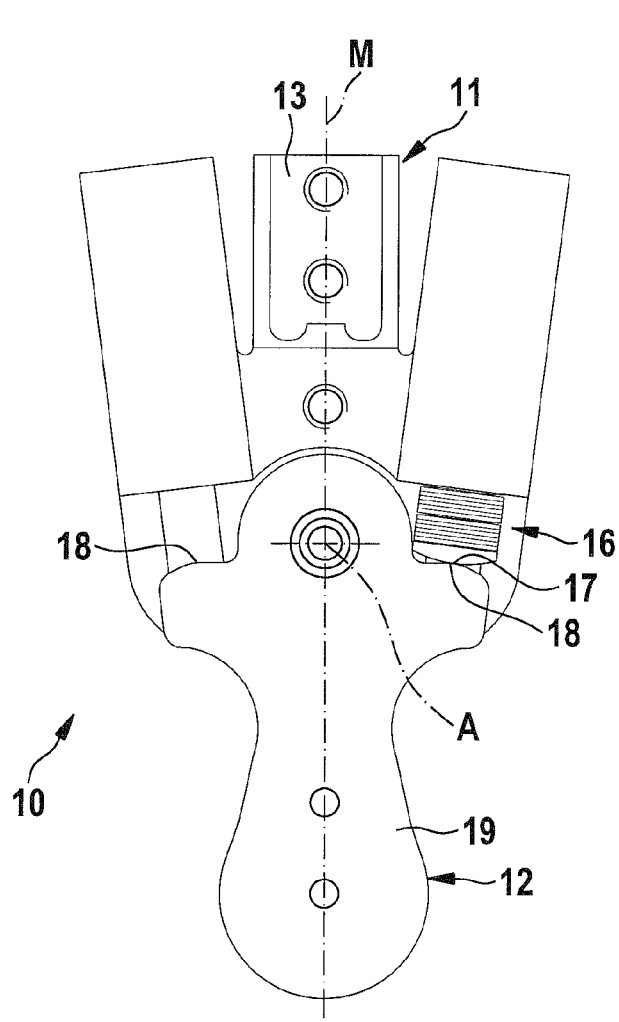
FIG. 1 shows a front view of the orthotic joint for ankle joints.
Figure 2:
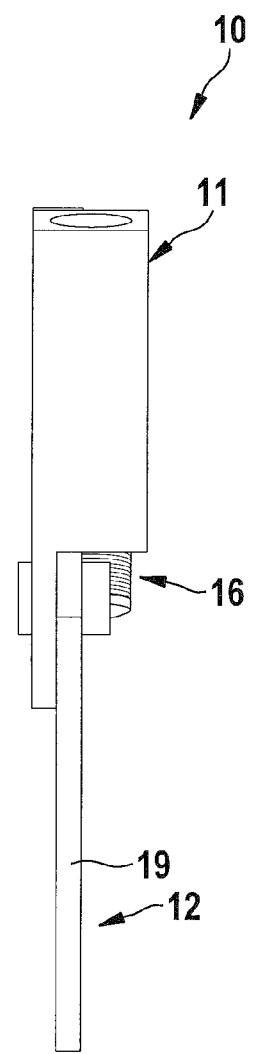
FIG. 2 shows a side view of the orthotic joint according to FIG. 1.
Figure 3:
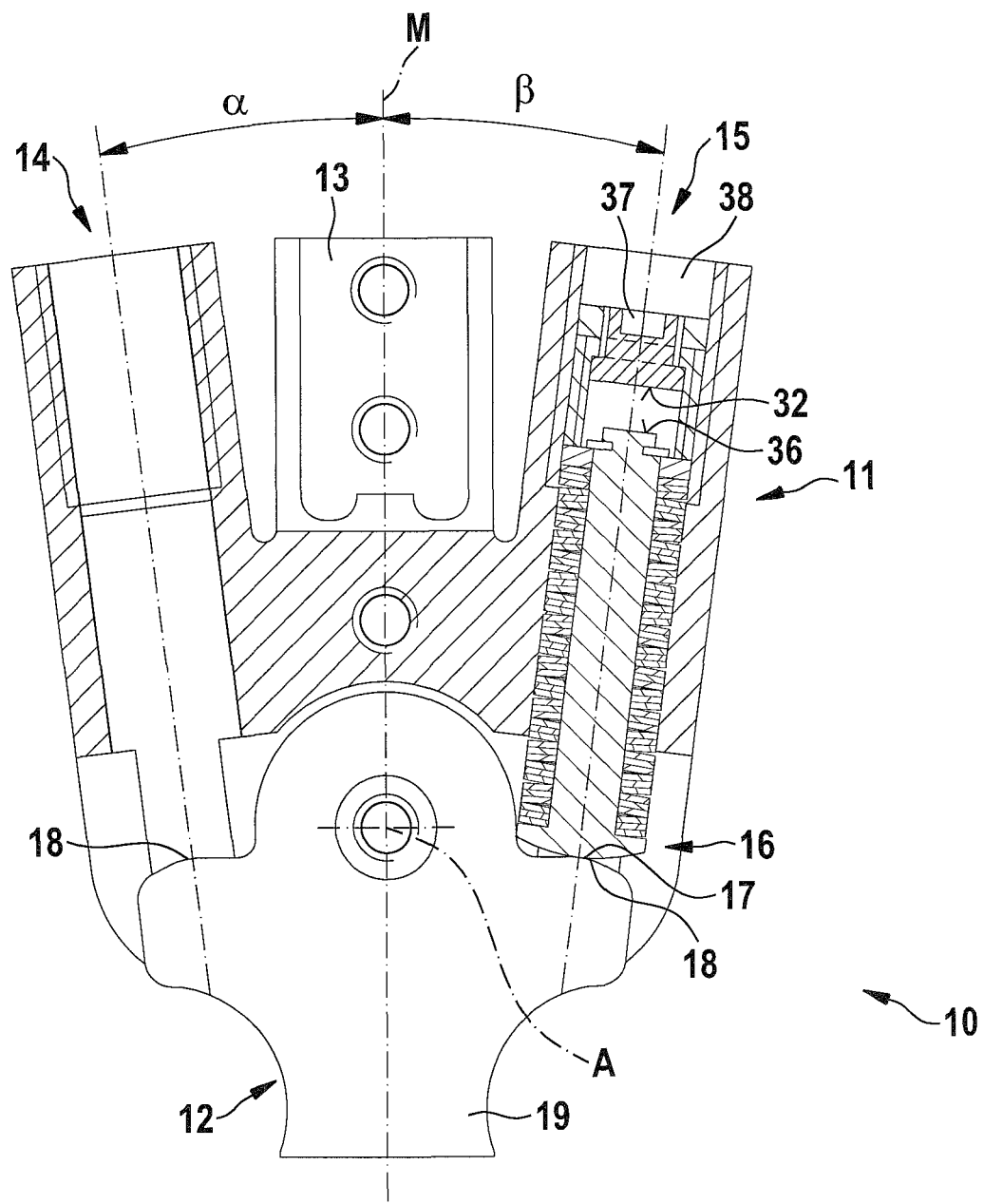
FIG. 3 shows a sectional view of the orthotic joint according to FIG. 1.

In the drawing, an orthotic joint is shown as an ankle joint for a leg orthosis. Of course the invention may also be used on other orthoses, such as for example arm orthoses or the like.

FIG. 1 shows schematically an orthotic joint 10 which comprises a joint part 11 and a stirrup 12. The stirrup 12 is arranged on the joint part 11 to be articulated or pivotable about an axis A or is connected to the joint part 11. The joint part 11 may be designed to have one part, for example as a base body, or multiple parts, for example as a base body with a cover, and has a splint mounting 13. The axis A is designed preferably centrally on the joint part 11 and on the stirrup 12 and preferably lies on the central axis M of the splint mounting 13. Of course the axis A may also be arranged off-centre or asymmetrically. The joint connection between the joint part 11 and the stirrup 12 may be produced to be releasable, for example by screws, non-releasable, for example by a rivet connection, or in a further conventional form.

The orthotic joint 10 is preferably constructed to be symmetrical, so that it may be used universally on the inside or outside or on the left or right. The joint part 11 likewise preferably constructed to be symmetrical has a channel 14, 15 on both sides of the axis A or central axis M. The channels 14, 15 run at an acute angle α and β to the central axis M and are designed and equipped to receive one function means 16, each. The channels 14, 15 themselves may be formed in the base body and/or in the cover of the joint part 11. One function means 16, each, for forming an abutment 17 is arranged in the channels 14, 15, wherein an abutment is formed as a front, dorsal abutment and an abutment is formed as a rear, plantar abutment for the stirrup 12 or its abutment surfaces 18. The stirrup 12, which is likewise preferably designed to be symmetrical, has, in addition to a strap 19 directed downwards from the axis A on both sides of the axis A, one dorsal or plantar abutment surface 18, each, depending on the installation direction of the orthotic joint 10. Using these abutment surfaces 18, the alignment of which may vary depending on the installation direction, the stirrup 12 can be pressed against the abutments 17 of the joint part 11. In other words, an operative connection can be produced if required or exists between the abutments 17 and the abutment surfaces 18. In the embodiment shown, for reasons of clarity, a function means 16 is shown only in one of the channels 14, 15, namely in channel 15.

The channels 14, 15 may be formed by simple bores. Other designs of channels 14, 15 are however likewise conceivable. The channels 14, 15 may be designed to be constant in their longitudinal extension with a constant diameter or, stepped or provided with shoulders, have different diameters. The diameter of the channels 14, 15 is at least as large as the diameter of the function means 16. The function means 16 are arranged firmly but releasably in the channels 14, 15 or attached in the latter, preferably by a screw connection. According to the invention, each function means 16 comprises a cup spring arrangement 20. The cup spring arrangements 20, which act on the stirrup 12, ensure that the lower leg of the patient is pressed again and again into the neutral function position and forms resilient dorsal abutments or plantar abutments 17.

The cup spring arrangement 20 (see in particular FIGS. 5 and 6) may consist of a single cup spring 21. However, the cup spring arrangement 20 preferably consists of several cup spring packets 22, wherein each cup spring packet 22 is formed from several cup springs 21. In the example shown, three cup springs 21 form a cup spring packet 22. In the embodiment shown, three cup springs 21, each, of a cup spring packet 22 are straightened, that is, with their convexly formed sides lying one against another (see in particular FIGS. 5 and 6). Adjacent-lying cup springs 22 each lie against one another alternating with their convexly or concavely formed sides. Other arrangements and combinations of cup spring packets 22 and of the cup spring arrangement 20 are however likewise possible. The number of cup springs 21 or of cup spring packets 22 may be varied in particular due to the modular structure of the cup spring packets 22 and of the cup spring arrangement 20.

In addition to the cup spring arrangements 20, each function means 16 comprises an expanding mandrel 23, an abutment element 24 and a securing element 25. The expanding mandrel 23 has a head element 26 and a shaft 27. The cup spring arrangement 20 is threaded onto the shaft 27 of the expanding mandrel 23, wherein the mushroom-shaped head element 26 serves as a stopper for the cup spring arrangement 20. The shaft 27 has at its free end a groove-like recess 28, into which the securing element 25, which may be for example a simple securing ring, engages. The cup spring arrangement 20 is pretensioned between the head element 26 and the securing element 25. The abutment element 24, which may be for example a simple washer, is likewise threaded onto the shaft 27 of the expanding mandrel 23 and is located between the cup spring arrangement 20 and the securing element 25.

The external diameter of the abutment element 24, for the formation of an abutment surface 29, is preferably greater than the external diameter of the securing element 25, so that the expanding mandrel 23 for the case that the abutment element 24 lies on an abutment which in the embodiment shown is formed by an adjusting element 30 for adjusting the plumb line, may plunge through the abutment element 24, as a result of which the spring tension of the cup spring arrangement 20 then clamped between the head element 26 and the abutment element 24 is increased.

The function means 16 comprises an adjusting element 31 for adjusting the freedom of movement and the adjusting element 30 already mentioned for adjusting the plumb line. Both adjusting elements 30, 31 are preferably designed as an adjusting screw. The adjusting element 30 for adjusting the plumb line is a cylindrical body having an external thread for attachment in the channel 14, 15 having an internal thread. The cylindrical body also has an internal thread for receiving the adjusting element 31 for adjusting the freedom of movement. The adjusting element 31 for adjusting the freedom of movement is a screw having an external thread for attachment in the adjusting element 30 for adjusting the plumb line and having an abutment surface 32 formed by the screw head for the expanding mandrel 23 or the abutment surface 36 formed on the free end of the expanding mandrel 23.

Figure 4:
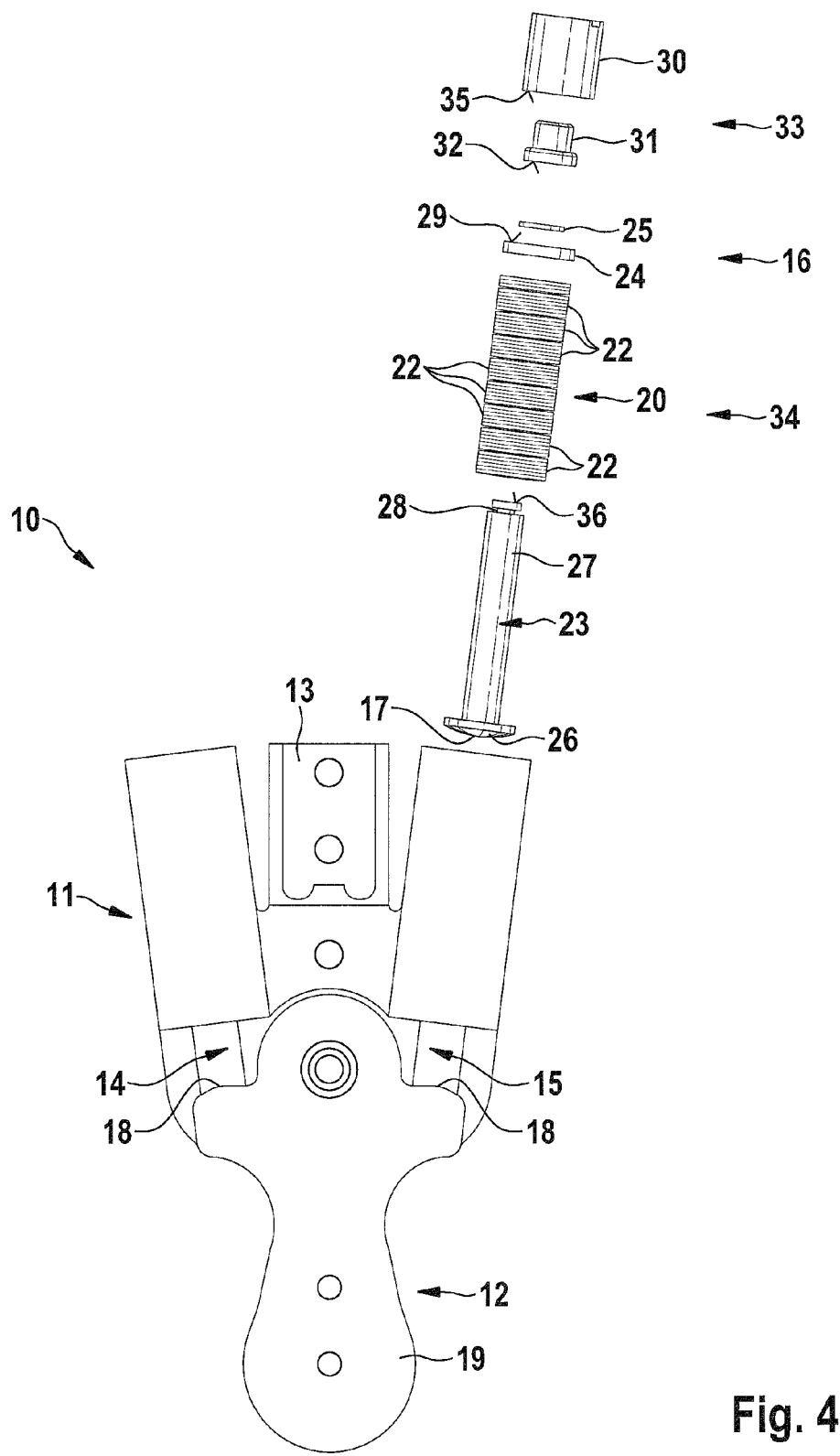
FIG. 4 shows the orthotic joint according to FIG. 1 with a function means in exploded representation.

The two adjusting elements 30, 31 form an adjusting unit 33 (see in particular FIG. 4), wherein the adjusting element 31 for adjusting the freedom of movement in the assembled state is arranged completely within the adjusting element 30 for adjusting the plumb line. The expanding mandrel 23 with the cup spring arrangement 20, the abutment element 24 and the securing element form a clamping unit 34. The adjusting unit 33 and the clamping unit 34 are preferably separate units which are not connected to one another, but which can be brought into or are in operative connection with one another. In further embodiments, the two units may also be connected to one another to form an overall unit.

The function means 16 in the embodiment shown is designed to be essentially cylindrical. The clamping unit 34 is placed preferably loosely and without connection to the joint part 11 in the channel 14, 15. The adjusting unit 33 is attached, namely preferably screwed, in the channel 14, 15 via the adjusting element 30 for adjusting the plumb line. The clamping unit 34 is thus held in the channel 14, 15. The adjusting unit 33 or more precisely the adjusting element 30 has on the side facing the function unit 34, an abutment surface 35 for resting of the abutment surface 29 of the abutment element 24. In further embodiments, the clamping unit 34 itself may be attached in the channel 14, 15. The possibility also exists of the function means 16 also being able to have different diameters over its longitudinal extension. In other words, the external diameters of the adjusting unit 33 and of the clamping unit 34 may be different.

The orthotic joint 10 is preferably a system joint and constructed in modular manner. This means that all individual parts or components of the orthotic joint 10 can be exchanged individually and in particular the clamping unit 34 can be adjusted to individual requirements by exchange and/or variation of the number of cup springs 21. The design and geometry of the orthotic joint 10 may also deviate from the embodiment shown. As mentioned, the channels 14, 15 run at an acute angle α and β to the central axis M of the joint part 11. The angles α and β are preferably the same size. However, the channels 14, 15 may also run at a different angle α≠β to the central axis M. In further embodiments, only one channel 14, 15 may also be provided with a function means 16.

When using the orthotic joint 10 according to the invention, it is usually initially fixed in the starting or function position, that is, is made stiff. The clamping unit 34 lies in the channel 14, 15. The adjusting unit 33 holds the clamping unit 34 in the channel 14, 15, in that the abutment element 24 with its abutment surface 29 is supported on the abutment surface 35 of the adjusting unit 33 or of the adjusting element 30. The exact function position is defined by the adjustment of the plumb line. Hence, the adjusting elements 30 are screwed into the channel 14 or 15. For the same position or screwing depth of the adjusting elements 30 on both sides of the axis A, a neutral 90° function position (90° between foot and lower leg) is adjusted. In the function position, the abutments 17 of the function means 16 lie on the abutment surfaces 18 of the stirrup 13 (see for example FIG. 1). If a forward leaning position of the patient is required, that is, for example an angle of 87° between foot and lower leg, the plantar adjusting element 30 can be screwed accordingly deeper in the channel 14, 15 than the dorsal adjusting element 30. For a backward leaning position, the dorsal adjusting element 30 can be screwed deeper in the channel 14, 15 compared to the plantar adjusting element 30, wherein plantar and dorsal can be reversed by rotating the orthotic joint 10.

The freedom of movement is adjusted by the adjusting element 31. To fix the orthotic joint 10, the abutment surface 36 of the function unit 34 or of the expanding mandrel 23 lies on the abutment surface 32 of the adjusting unit 33 or of the adjusting element 31 for adjusting the freedom of movement. Hence, the adjusting element 31 is rotated so far out of the adjusting element 30 (without projecting from the adjusting element 30) that a distance no longer exists between the expanding mandrel 23 and the adjusting element 31. By screwing the adjusting element 31 into the adjusting element 30, that is by increasing the distance between the abutment surfaces 36 and 32, the freedom of movement is released bit by bit, wherein the movement (dorsal extension and plantar flexion) triggered by walking is then effected against the spring force of the cup spring arrangement 20. Since the abutment element 24 of the clamping unit 34 cannot get out of the way, since it rests with its abutment surface 29 on the abutment surface 35 of the adjusting unit 33, the expanding mandrel 23 abuts or plunges through the abutment element 24 until it is stopped by the abutment surface 32 of the adjusting element 31 as a movement boundary. As soon as the pressure on the cup spring arrangement 20 decreases or is removed, the cup spring arrangement 20 presses the lower leg into the previously selected or adjusted function position for a secure standing position. The extent of the freedom of movement may then be changed by readjusting the adjusting element 31, that is, by changing the distance between the adjusting element 31 and the expanding mandrel 23. The readjustment may be executed, for example by a square socket 37 or the like formed in the adjusting element 31, for which the adjusting element 30 has an access opening 38 to the adjusting facility.

The invention claimed is:

1. Orthotic joint, in particular ankle joint for a leg orthosis, comprising a joint part with a splint mounting and a stirrup which is connected to the joint part to be pivotable about an axis A and has a dorsal and a plantar abutment surface, wherein on both sides of the axis A, on the joint part is formed a channel, in which one function means, each, for forming a dorsal or plantar abutment for the stirrup or its abutment surfaces is arranged, characterised in that each function means comprises a cup spring arrangement.

2. Orthotic joint according to claim 1, characterised in that the cup spring arrangement consists of several cup spring packets, wherein each cup spring packet is formed from several cup springs.

3. Orthotic joint according to claim 1, characterised in that each function means comprises an adjusting element for adjusting the freedom of movement and an adjusting element for adjusting a plumb line.

4. Orthotic joint according to claim 1, characterised in that each function means comprises an expanding mandrel, an abutment element and a securing element.

5. Orthotic joint according to claim 4, characterised in that the cup spring packets are threaded onto the expanding mandrel and pretensioned between a head element of the expanding mandrel and the securing element.

6. Orthotic joint according to claim 5, characterised in that the abutment element is a washer which is likewise threaded onto the expanding mandrel and is located between the cup spring arrangement and the securing element.

7. Orthotic joint according to claim 3, characterised in that the adjusting element for adjusting the plumb line is an adjusting screw having an external thread for attachment in the channel having an internal thread and is provided with an internal thread for receiving the adjusting element for adjusting the freedom of movement.

8. Orthotic joint according to claim 7, characterised in that the adjusting element for adjusting the freedom of movement is an adjusting screw having an external thread for attachment in the adjusting element for adjusting the plumb line and has an abutment surface for the expanding mandrel.

9. Orthotic joint according to claim 8, characterised in that the adjusting element for adjusting the plumb line and the adjusting element for adjusting the freedom of movement form an adjusting unit, wherein the adjusting element for adjusting the freedom of movement in the assembled state is arranged completely within the adjusting element for adjusting the plumb line.

10. Orthotic joint according to claim 4, characterised in that the expanding mandrel with the cup spring arrangement, the abutment element and the securing element form a clamping unit.

11. Orthotic joint according to claim 10, characterised in that the clamping unit and the adjusting unit are separate units which can be brought into operative connection with one another.

12. Orthotic joint according to claim 1, characterised in that the orthotic joint is a modular system joint.

* * * * *